United States Patent [19]

Berris

[11] Patent Number: 5,030,757

[45] Date of Patent: Jul. 9, 1991

[54] PHASE TRANSFER CATALYST RECOVERY

[75] Inventor: Bruce C. Berris, Baton Rouge, La.

[73] Assignee: Ethyl Corporation, Richmond, Va.

[21] Appl. No.: 519,744

[22] Filed: May 7, 1990

[51] Int. Cl.$^5$ ............................................. C07C 209/86
[52] U.S. Cl. ..................................... 564/296; 564/281
[58] Field of Search ................................. 564/296, 281

[56] References Cited

U.S. PATENT DOCUMENTS

| | | | |
|---|---|---|---|
| 3,148,214 | 9/1964 | Smith | 564/296 |
| 3,523,967 | 8/1970 | Dewar et al. | 564/296 |
| 3,579,581 | 5/1971 | Maloney et al. | 564/296 |
| 3,992,432 | 11/1976 | Napler et al. | 260/465.1 |
| 4,172,782 | 10/1979 | Masuko et al. | 564/296 |
| 4,489,698 | 12/1984 | Idel et al. | 564/281 |

FOREIGN PATENT DOCUMENTS 55571  5/1968  Poland ................................. 570/160

OTHER PUBLICATIONS

"Preliminary Study on the Role Played by the Third Liquid Phase in Phase Transfer Catalysis" by Der-Her Wang and Hung-Shan Weng, *Chemical Engineering Science*, vol. 43, No. 8, pp. 2019-2024, 1988.

*Primary Examiner*—James H. Reamer
*Attorney, Agent, or Firm*—David M. Bunnell

[57] ABSTRACT

A quaternary ammonium salt catalyst is recovered from mixtures where the salt is in contact with an aqueous alkaline phase by adding water to completely dissolve the salt and adding base to cause the dissolved catalyst to separate as a hydroxide which forms an oily upper phase.

8 Claims, No Drawings

PHASE TRANSFER CATALYST RECOVERY

BACKGROUND

This invention relates generally to the recovery of quaternary ammonium salts from aqueous solutions and more particularly to the recovery of quaternary ammonium salt, phase transfer catalysts from reaction mixtures resulting from the alkylation of cyclopentadienes.

The preparation of monosubstituted cyclopentadiene derivatives by condensation with corresponding halogen compounds such as alkyl halides in the presence of a condensing agent such as aqueous alkali metal hydroxide and small amounts (below about 0.1 mole per mole of cyclopentadiene) of quaternary ammonium compounds, which catalyze the reaction, is described in Polish Patent 55,571.

I have found an effective method for recovering the catalyst which permits its reuse and also avoids its discharge in the aqueous waste stream from the reaction.

BRIEF SUMMARY

In accordance with this invention, there is provided a process for recovering a quaternary ammonium salt from a mixture wherein said salt is in contact with an aqueous alkaline phase comprising the steps of (a) adding water to said mixture to completely dissolve said salt, and (b) adding base to cause the dissolved quaternary ammonium salt to separate as a hydroxide which forms an oily upper phase.

In one aspect of the process, a quaternary ammonium salt, phase transfer catalyst is recovered from a reaction mixture resulting from the preparation of cyclopentadiene derivatives by the reaction of cyclopentadiene with an organic halide in the presence of aqueous base and said catalyst, comprising the steps of (a) allowing said mixture to settle into an upper organic phase, a lower aqueous phase and an intermediate quaternary ammonium catalyst phase (b) removing said organic phase (c) adding water to said remaining mixture to completely dissolve said catalyst phase, and (d) adding base to cause the dissolved quaternary ammonium salt to separate as a hydroxide which forms an oily upper phase.

In another aspect of the invention, water is added such that the water solution of the quaternary ammonium salt forms a separate layer on top of the lower aqueous phase and the water solution is separated from the lower phase before adding base.

Quaternary ammonium compounds are known in the art and are described, for example in Kirk-Othmer, Encyclopedia of Chemical Technology, Vol. 19, pages 521-531 Third Edition (1982). The salts can be represented by the formula:

$$R_4N^+X^-$$

where R can be the same or different $C_1$ to about $C_{18}$ hydrocarbyl groups and the anion $X^-$ is an anion which will dissociate from the cation in an aqueous environment and is preferably halogen, and more particularly chloride, bromide, iodide, or hydroxyl. Examples of quaternary ammonium salts suitable for use as phase transfer catalysts include, tri-n-butyl-methylammonium chloride, phenyltrimethylammonium bromide, tetra-n-butylammonium bromide, tetraethylammonium chloride, triethylbenzylammonium chloride, ethyltrimethylammonium iodide, trimethyloctodecylammonium chloride, trimethyldodecylammonium chloride, tetra-n-propylammonium chloride, methyltrioctylammonium chloride and the like.

The phase transfer catalysts are useful in preparing mono-substituted cyclopentadiene derivatives. Such derivatives, such as $C_1$ to about $C_{12}$ alkylcyclopentadienes, are useful intermediates in the preparation of transition metal cyclopentadienyl carbonyl compounds such as methylcyclopentadienylmanganese tricarbonyl which is used as a gasoline antiknock compound.

The cyclopentadiene derivatives can be represented, for example, by the formula:

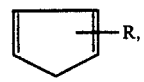

where R is a $C_1$ to about $C_{20}$ hydrocarbyl group such as a saturated or unsaturated alkyl substituent, an aralkyl or alkyl substituent substituted with an ether, ester, cyanide, dialkylamine group or halogen atom, or R denotes a cyclic radical containing 2 methylene groups located in position 5 of the cyclopentadiene ring. The R group may also be a chain linking two cyclopentadiene rings.

The cyclopentadienyl derivatives are formed by condensation of cyclopentadiene with from about 0.5 to 2 mole of a halide of the formula R-X per mole of cyclopentadiene, where R has the above-cited meaning and X denotes Cl or Br, and in the case of production of derivatives containing a cyclopropyl radical, cyclopentadiene is condensed with halides of the formula $X(CH_2)_nX$, in which X has the above cited meaning and $n=2$. In cases where a dicyclopentadienyl derivative is produced, X has the above meaning and $n = 3$ or more.

The reaction is carried out in the presence of aqueous base such as alkali or alkaline earth metal hydroxides as condensation agents and in the presence of small amounts of quaternary ammonium compounds that are effective to catalyze the reaction, for example amounts of from about 0.001 to 1 mole of catalyst per mole of cyclopentadiene. Use of amounts of at least about 0.008 mole per mole of cyclopentadiene not only provides good reaction rates and yields but also results in the separation of most of the catalyst as a viscous third phase between the organic product containing phase and the lower aqueous phase.

The base, condensation agents are preferably added as concentrated aqueous solutions. Useful bases include, for example, alkali or alkaline earth metal hydroxides. Preferred bases are about 25 to 50 wt % aqueous sodium hydroxide and solid sodium or potassium hydroxide.

The cyclopentadiene can be reacted neat or diluted with about 5 to 100 wt %, based on the wt % of cyclopentadiene, of an inert organic solvent such as, for example, benzene, or a $C_6$ to $C_{10}$ hydrocarbon such as hexane, cyclohexane, heptane, octane or decane and the like. The reaction temperature can vary from below to above normal room temperature and preferably is from about 10° to 50° C. Times to complete the reaction usually range from about 0.5 to 6 hours.

After the reaction is completed, the reaction mixture is allowed to settle into an upper organic phase and a lower aqueous, alkaline suspension of alkali metal halide. A third phase is usually observed at the interface between the upper and lower phases which is a viscous liquid consisting mostly of the quaternary ammonium catalyst. The organic phase can be decanted off for product recovery such as by distillation. the lower phase to leave mostly catalyst phase clinging to the I have found that it is possible to carefully draw off walls of the reactor which can be used in situ to catalyze the preparation of a second batch of cyclopentadiene derivative. However, complete removal of the thick slurry of alkali metal salt in the aqueous alkaline phase can be difficult, especially from a commercial scale reactor, and it also desirable to know the amount of catalyst remaining in the reactor. This is difficult to estimate, especially considering that the third phase does not have sharp interfaces with the other phases and the catalyst phase is impure and does not contain all of the original catalyst. I have found that if sufficient water is added to the reactor, such that the hydroxyl ion concentration in the aqueous phase is reduced below about 2 molar, then a homogeneous aqueous solution containing the dissolved quaternary ammonium catalyst results. Upon treatment of this solution with concentrated aqueous base such as 50 to 100 wt % aqueous NaOH, the quaternary ammonium catalyst will separate as its hydroxide to form an oily upper layer which can be removed either by decantation or by drawing off the lower aqueous phase. In this way, the organics are removed from the aqueous waste stream and the quaternary ammonium catalyst is recovered for recycle.

I have also discovered that it is not necessary to add sufficient water to form a single homogenous phase but that the catalyst can be efficiently recovered by adding only sufficient fresh water (about 2 to 10 ml H$_2$O per ml of catalyst) to dissolve the catalyst phase, without disturbing the lower alkaline salt slurry such that the pH of the added water is not raised significantly. The separate aqueous phase containing the catalyst can then be separated such as by decantation and the catalyst recovered from the water solution by raising the pH of the solution with base so that the quaternary ammonium hydroxide separates an an oil layer. This is more economical because a smaller amount of base is used than in the method described above.

The organic product phase can be washed with water and the water washings added to the aqueous, quaternary ammonium salt solution to recover any catalyst that was removed with the organic product phase.

The process of the invention is further illustrated by, but is not intended to be limited to, the following examples.

EXAMPLE 1

To a 300 ml stainless steel autoclave, equipped with cooling coils and magnetic stirring, are charged under nitrogen 40 ml (60 g) of 50 wt % NaOH (0.75 mol), 2 ml of 85 wt % tri-n-butylmethylammonium chloride (0.0072 mol), 38.0 ml of cyclopentadiene (0.576 mol) and 1.82 g of octane as an internal standard for analysis by gas chromatography. At a temperature of 18° C. the charging of 20.8 g (0.42 mol) of methylchloride is started by evaporation from a charging bomb. The reactor is cooled to maintain the desired temperature of 35° C. After 2 hours the reaction is complete. About 100 ml of water is then added. The reaction mixture is allowed to settle and a third, dark purple liquid phase of about 2 ml in volume is observed between the organic and aqueous phases. The organic phase (41.2 g) is decanted off and is washed with water. The organic phase contains about 13.0 grams of cyclopentadiene, 24.9 grams of methylcyclopentadiene and minor amounts of other methylcyclopentadienes and dicyclopentadiene. Conversion is 66%. The dark purple liquid phase is dissolved in fresh (not basic) water (10 ml) without disturbing the lower aqueous/NaCl slurry. The upper phase is removed and combined with the water wash from the organic layer. These combined aqueous extracts (about 25 ml) are added to 50 ml of 50% aqueous NaOH and a purple oil separates which is used to successfully catalyze a second preparation of methylcyclopentadiene.

EXAMPLE 2

To illustrate the recovery of catalyst by forming a homogeneous mixture with the lower phase, an aqueous, alkaline NaC$_1$ suspension is prepared by mixing 15.8 grams NaC$_1$ (0.27 mol), 16.5 grams water, and 11.2 grams of 50% NaOH solution (0.13 mol). Tri-n-butylmethylammonium chloride (85% aqueous solution, 0.98 g, 0.83 gram of contained salt, 3.5 mmol is added which forms an upper, yellow phase. The entire mixture is dissolved to form one homogeneous phase by adding 42 ml water. To this mixture, 7 grams of NaOH pellets are added. A yellow, upper phase appears which is removed using a pipette. The material weighs 1.05 grams and contains 0.65 grams of tri-n-butylmethylammonium hydroxide (3.0 mmol). The recovery is 85% of theoretical.

I claim:

1. A process for recovering a quaternary ammonium salt of the formula $R_4N^+X^-$, where R is the same or different C$_1$ to about C$_{18}$ hydrocarbyl groups and $X^-$ is halogen or hydroxyl, from a mixture wherein said salt is in contact with an aqueous alkaline phase, comprising the steps of (a) either (i) adding about 2 to 10 ml of water per ml of salt to said mixture to completely dissolve said salt, such that the water solution of said salt remains as a separate layer on top of said aqueous alkaline phase and separating said layer from the lower aqueous alkaline phase or, (ii) adding sufficient water such that the hydroxyl ion concentration in the aqueous alkaline phase is reduced to below about 2 molar so as to form a single phase solution of said salt, and (b) adding base to raise the pH of the solution of said salt so as to cause the dissolved quaternary ammonium salt to separate as a hydroxide which forms an oily upper phase.

2. The process of claim 1 wherein said mixture comprises an oily catalyst phase containing said quaternary ammonium salt in contact with a lower phase which comprises a suspension of an alkali or alkaline earth metal halide salt in aqueous alkali or alkaline earth metal hydroxide, about 2 to 10 ml of water per ml of catalyst is added such that the water solution of said quaternary ammonium salt remains as a separate layer on top of said lower phase, and said water solution is separated from said lower phase prior to adding said base.

3. The process of claim 1 wherein said mixture comprises an oily phase containing said quaternary ammonium salt in contact with a lower phase which comprises a suspension of an alkali or alkaline earth metal halide salt in aqueous alkali or alkaline earth metal hydroxide and sufficient water in step (a) is added to reduce the hydroxyl ion concentration in said lower phase to below about 2 molar such that the water solution of said quaternary ammonium salt and said lower phase form one homogeneous phase.

4. A process for recovering a quaternary ammonium salt, phase transfer catalyst having the formula $R_4N^+X^-$, where R is the same or different C$_1$ to about C$_{18}$ hydrocarbyl groups and $X^-$ is halogen or hydroxyl, from the reaction mixture resulting from the preparation of cyclopentadiene derivatives by the reaction of cyclopentadiene with an organic halide in the presence of aqueous base and at least about 0.008 mole of said catalyst per mole of cyclopentadiene, comprising the steps of (a) allowing said mixture to separate into an upper organic phase, a lower aqueous alkaline phase and an intermediate catalyst phase (b) removing said upper organic phase (c) either (i) adding about 2 to 10 ml of water per ml of catalyst to said remaining phases to completely dissolve said salt, such that the aqueous solution of said salt and added water remains as a separate layer on top of said lower aqueous alkaline phase and separating said layer from said lower aqueous alkaline phase or, (ii) adding sufficient water to said remaining phases such that the hydroxyl ion concentration in said lower aqueous alkaline phase is reduced to below about 2 molar so said remaining phases form a single phase, aqueous solution of said salt and (d) adding base to raise the pH of said aqueous solution so as to cause the dissolved quaternary ammonium salt to separate as a hydroxide which forms an oily upper phase.

5. The process of claim 4 wherein, after removal, said upper organic phase is extracted with water and said water extract is added to said dissolved quaternary ammonium salt.

6. The process of claim 4 wherein the recovered catalyst is used to catalyze a second preparation of cyclopentadiene derivatives.

7. The process of claim 4 wherein said water is added such that the water solution of said quaternary ammonium salt remains as a separate layer on top of said lower aqueous phase, and said water solution is separated from said lower aqueous phase prior to adding said base.

8. The process of claim 4 wherein said lower aqueous phase comprises a suspension of an alkali or alkaline earth metal halide salt in aqueous alkali or alkaline earth metal hydroxide and sufficient water is added in step (c) to reduce the hydroxyl ion concentration in said lower phase to below about 2 molar such that the water solution of said quaternary ammonium salt and said lower phase form one homogeneous phase.

* * * * *